United States Patent [19]

Baudino

[11] Patent Number: 5,702,437

[45] Date of Patent: Dec. 30, 1997

[54] IMPLANTABLE LEAD WITH WIRES CARRIED BY BODY

[75] Inventor: Michael D. Baudino, Coon Rapids, Minn.

[73] Assignee: Medtronic Inc., Minneapolis, Minn.

[21] Appl. No.: 630,442

[22] Filed: Apr. 10, 1996

[51] Int. Cl.$^6$ ............................................. A61N 1/05
[52] U.S. Cl. ................................................. 607/116
[58] Field of Search ........................... 607/116, 117,
607/118, 119, 120, 121, 122, 123, 124,
125, 126, 127, 128, 129, 130, 132, 133,
134, 135, 136, 137, 138; 128/142

[56] References Cited

U.S. PATENT DOCUMENTS

| | | | |
|---|---|---|---|
| 4,832,051 | 5/1989 | Jarvik et al. | 607/116 |
| 5,228,441 | 7/1993 | Lundquist | 607/116 |
| 5,324,321 | 6/1994 | Pohndorf et al. | 607/116 |
| 5,417,208 | 5/1995 | Winkler | 607/122 |
| 5,483,022 | 1/1996 | Mar | 174/128.1 |

*Primary Examiner*—William E. Kamm
*Attorney, Agent, or Firm*—Banner & Witcoff, Ltd.

[57] ABSTRACT

An implantable lead having a body defining an uneven outer surface and a wire carried by the outer surface to form convolutions arranged so that portions of each convolution are displaced from the outer surface. The body may include a hollow core which carries beads so that stretching in the direction of a central axis is inhibited and drug infusion is facilitated. Alternatively, the body may take the form of a helix so that stretching of the lead in the direction of the central axis is facilitated.

19 Claims, 3 Drawing Sheets

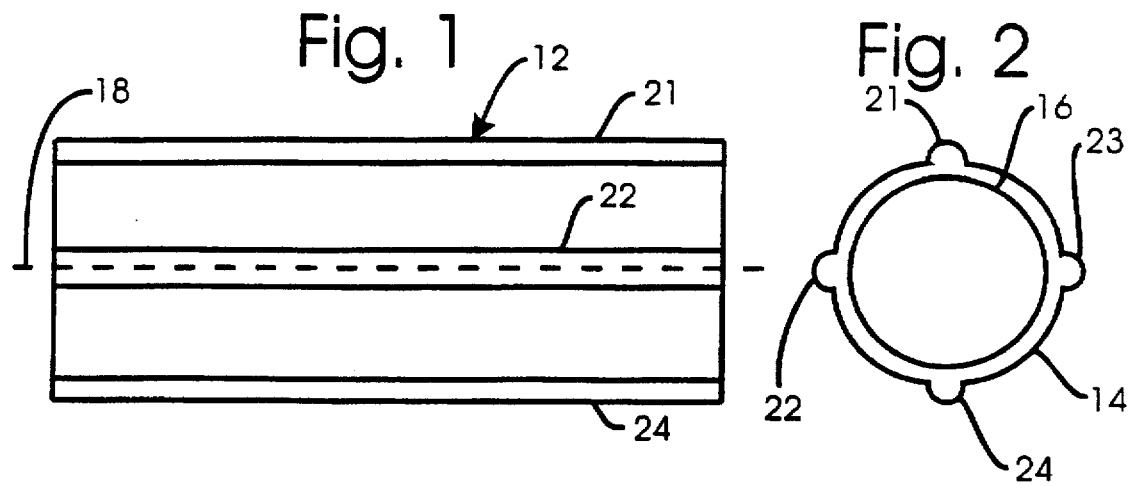
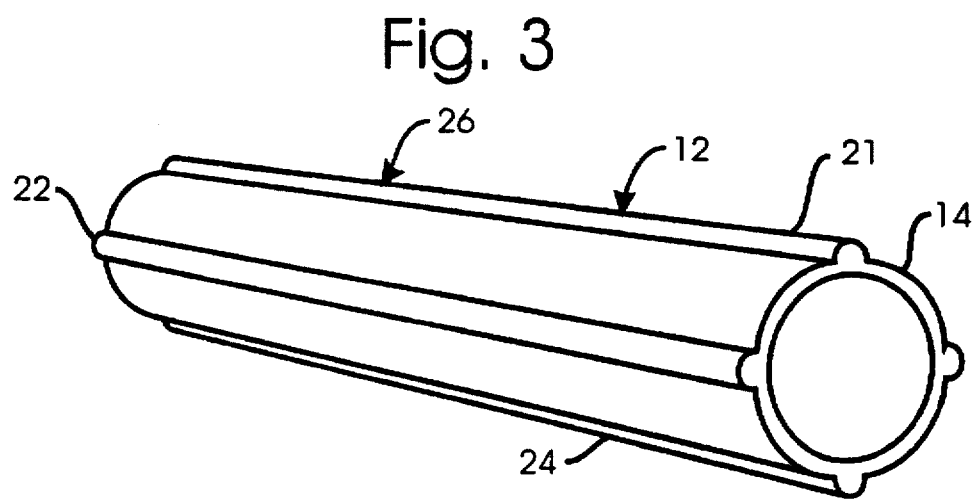

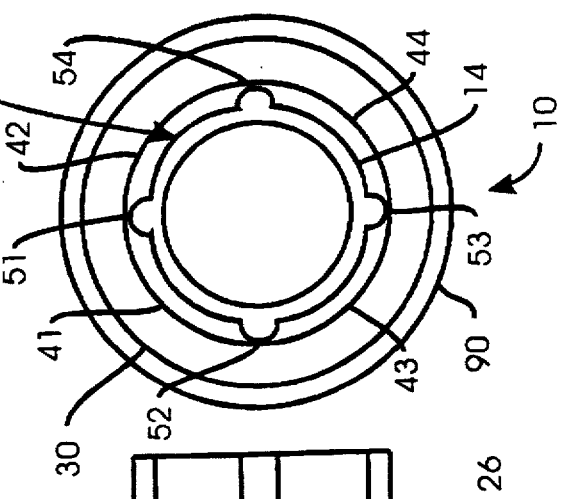
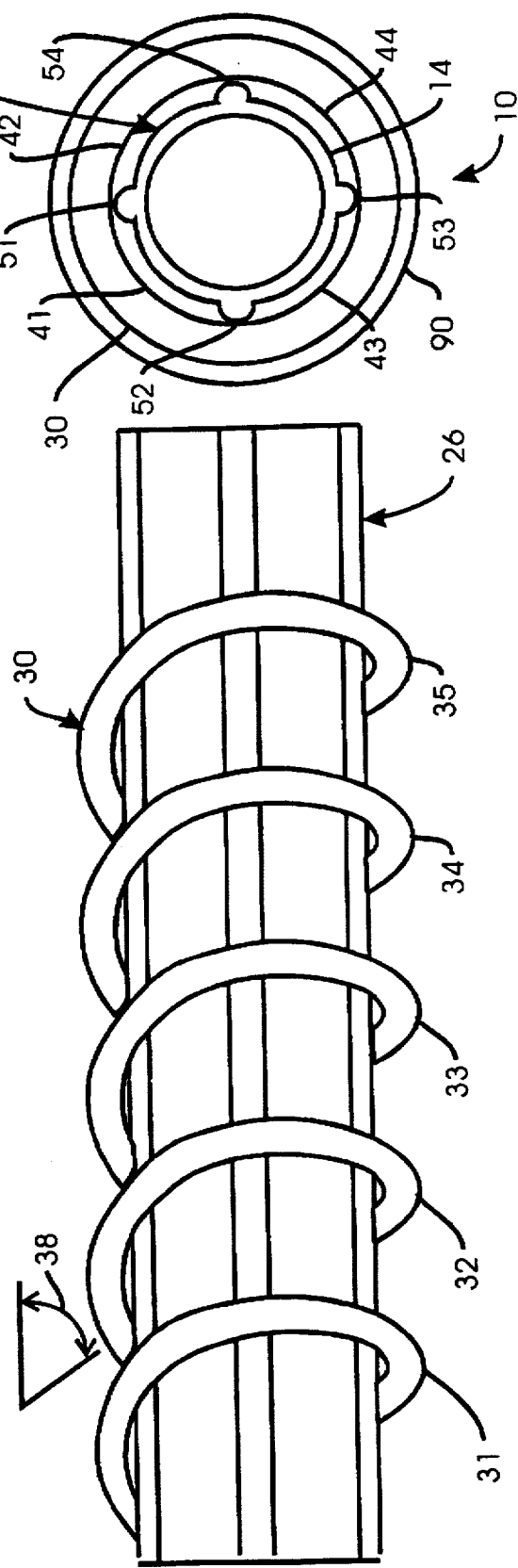

IMPLANTABLE LEAD WITH WIRES CARRIED BY BODY

BACKGROUND OF THE INVENTION

1. Field of the Invention

This invention relates to implantable leads and more particularly relates to such leads for carrying electrodes suitable for stimulation of living tissue and infusing drugs suitable for therapy.

2. Description of the Related Art

Most implantable leads utilized today are based on coiled spring designs. In such leads, the wire used to connect the lead to electrodes is wrapped around a mandrel with enough tension to cause the wire to exceed its yield point and thus to hold a coiled shape. Leads having a high pitch, that is leads in which there are a low number of convolutions per inch, are difficult to fabricate with the foregoing technique and the flex fatigue life is adversely affected by the pitch.

In designs based on a coiled spring approach, the resistance of the coiled leads is generally high due to the length of the wire needed to form the coils. By increasing the pitch of the wire, less material is needed to form the coil which results in a decrease in electrical resistance. However, the insulation on the wire is susceptible to "breakage" due to the process of coiling and due to the tension needed to cause the wire to exceed its yield point in order to form the coil.

Other implantable leads utilize stranded "cable" wire. In such leads, the individual strands are very small and have relatively good flex fatigue when used in a linear fashion. However, the wire does not hold its shape, which increases the difficulty of implanting a lead using such wire. The present invention is directed to solving these problems.

SUMMARY OF THE INVENTION

According to a preferred form of the invention, a body defines an uneven outer surface. Wire is carried by the outer surface to form convolutions arranged so that portions of each convolution are displaced from the outer surface. An outer covering is located around the body and the wire whereby the body provides sufficient stiffness for implantation so that the wire can be selected for improved flex fatigue life.

According to another embodiment of the invention, the body comprises a core that defines a central lumen and support members carried by the body that define the uneven outer surface. According to this embodiment, the core generally defines a hollow cylinder having a central axis whereby stretching in the direction of the central axis is inhibited.

According to another embodiment of the invention, the body generally defines a helix having convolutions arranged in a first direction and having a central axis, whereby stretching of the lead in the direction of the central axis is facilitated.

By using the foregoing techniques, the ease of implantation and reliability of an implantable lead can be increased for both electrical stimulation and drug infusion.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1 is a side top plan, fragmentary view of a preferred form of lead body made according to the invention;

FIG. 2 is an end view of the lead body shown in FIG. 1;

FIG. 3 is a perspective view of the lead body shown in FIG. 1;

FIG. 4 is a view like FIG. 1 with a wire wrapped around the body;

FIG. 5 is an end elevational view of the portion of the lead shown in FIG. 4 with an outer covering in place.

DESCRIPTION OF THE PREFERRED EMBODIMENTS

Figure 6:
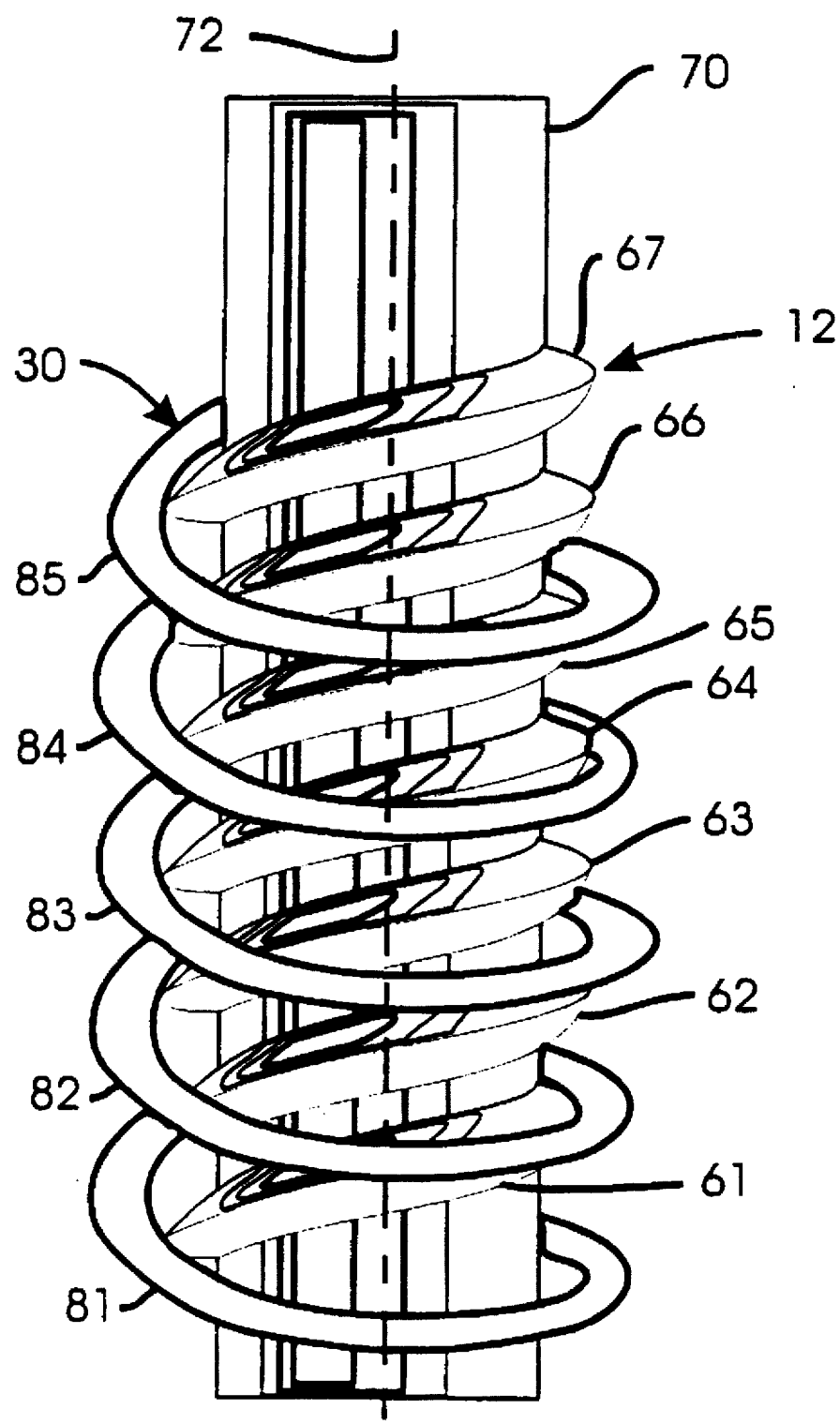
FIG. 6 is a top plan view of an alternative embodiment of the invention mounted on a fabricating mandrel.

Referring to FIG. 5, a preferred form of the invention basically includes an implantable lead 10 having a body 12 around which is wrapped a wire 30. An outer covering 90 is located around the body and wire.

Referring to FIGS. 1–3, body 12 comprises a generally cylindrical core 14 defining an inner surface 16 that forms a lumen in the shape of a cylinder having a central axis 18. Alternatively, core 14 may be solid. Core 14 also includes support members in the form of beads 21–24 that are aligned parallel to axis 18 and which form semicircles in cross-section. Beads 21–24 are integrally formed with core 14 which is fabricated from a solvent, heat or adhesive compatible material, such as polyethylene, various fluorocarbons, such as Teflon PFA (perfluoroalkoxy), urethanes, etc., that are considered acceptable for long-term implantable use. Drugs may be infused into a patient's body through the lumen. A stylet may be inserted into the lumen to add stiffness useful during implantation.

Referring to FIG. 4, core 14 and beads 21–24 form an uneven outer surface 26 on which a wire 30 is wound to form convolutions, such as 31–35. Referring to FIG. 5, convolutions 31–35 each have portions, such as 41–44, displaced from surface 26. The convolutions make contact with beads 21–24 forming nodal intersection points 51–54.

Wire 30 is preferably fabricated from multistrand wire cable coated with an insulation fabricated from a material compatible with bonding to core 14. For example, both the core 14 and the coating of wire 30 could be fabricated from a fluorocarbon, such as Teflon PFA. Wire 30 is coiled around core 14 with insufficient tension to cause the wire material to exceed its yield point, yet is held in intimate contact with beads 21–24 of core 14. This is an important feature which substantially adds to the flex fatigue life of the lead and also allows for high pitch coils to be fabricated.

The embodiments shown in FIGS. 1–5 resist stretching in the direction of axis 18. For some applications this is an important feature. As shown in FIG. 5, body 12 and wire 30 are covered by a conventional jacket 90 fabricated from materials generally considered acceptable for long term implantable use, typically polyurethane or silicone rubber. The diameter of wire 30 is approximately in the range of 0.002 inch to 0.012 inch. The pitch angle 38 (FIG. 4) of the convolutions shown in FIG. 4 is in the range of 10 degrees to approaching 90 degrees. At 10 degrees the helical coil approaches a straight or linear wire whereas when it approaches 90 degrees the helical coil would be considered tight or close wound. Typically, wire 30 is connected to one electrode to provide electrical stimulation of tissue after the lead is implanted in the patient, but multiple wires could be utilized to connect to multiple electrodes forming independent circuits, i.e., multiconductor leads.

In order to fabricate the embodiments shown in FIGS. 1–5, the wire is bonded to beads 21–24 at each intersection of the wire insulation and beads forming nodal connections. The point of attachment holds wire 30 in the desired shape and acts as a hinge to allow the wire to move when in tension, compression, or bending. This is an important feature which facilitates implantation of lead 10 in a patient. The bonding of the joints can be accomplished by methods compatible with the base materials used for the coating on wire 30 and the core 14. One method would be heat bonding where the heat application zone may include the entire length of the body 12 or be in specific areas. The heat application may be by convection in an oven or by infrared heating. Similar methodologies could be used for solvent or adhesive bonding of the joints.

Those skilled in the art can select the relationship between the number of beads and the pitch of wire 30. Generally, the greater the pitch of wire 30, the fewer beads are required. Very long pitches may require more beads to give sufficient attachment points to properly support wire 30. After the insulation of wire 30 is successfully bonded to body 12, jacket 90 is placed over coil 30 by conventional methods.

Referring to FIG. 6, an alternative embodiment of the invention comprises body 12 in the form of convolutions 61–67 that are formed in a clockwise direction. Convolutions 61–67 are shown mounted on a mandrel 70 that defines a cylinder having a central axis 72. Mandrel 70 is used to form convolutions 61–67 in a conventional manner. The mandrel is withdrawn after the fabrication process is complete, thereby forming a hollow lumen in body 12. A stylet may be inserted in the lumen, and drugs may be infused through the lumen. Alternatively, a thin walled tube could replace the forming mandrel allowing a closed conduit from proximal to distal ends of body 12. The core convolutions would "float" on the inner conduit formed by the thin walled tube. Drugs may be infused through the thin walled tube.

Convolutions 61–67 are shown with a triangular cross section. However, convolutions with a circular, rectangular or elliptical cross section also can be used. The pitch of convolutions 61–67 preferably is in the range described previously.

Convolutions 81–85 of wire 30 are wound around the outside of convolutions 61–67 in a counterclockwise direction opposite the clockwise direction of convolutions 61–67. Heat treating fuses the points of contact of convolutions 61–67 and 81–85 in the same manner described in connection with FIGS. 1–5. Convolutions 81–85 preferably have a pitch approximately equal to that of core 12 convolutions 61–67. An outer covering can be placed over convolutions 61–67 and 81–85 in the same manner as covering 90 shown in FIG. 5.

The embodiment shown in FIG. 6 enables stretching in the direction of axis 72. For some applications where lead elongation could be a factor, this embodiment provides the necessary lead compliance to eliminate failures due to tensile mode breaks and/or reduces the lead movement at the electrodes, eliminating the need to reposition the lead due to dislodgement.

Those skilled in the art will recognize that the preferred embodiments may be altered or amended without departing from the true spirit and scope of the invention, as defined in the accompanying claims.

I claim:

1. An implantable lead comprising:

a body defining an uneven outer surface;

wire carried by said outer surface to form convolutions arranged so that portions of each convolution are displaced from said outer surface; and an outer covering located around said body and wire, whereby said body provides sufficient stiffness for implantation so that said wire can be selected for improved flex fatigue life.

2. A lead, as claimed in claim 1, wherein said body is solid.

3. A lead, as claimed in claim 1, wherein said body comprises:

a core defining said central lumen; and support members carried by said body defining said interrupted outer surface.

4. A lead, as claimed in claim 3, wherein said core generally defines a hollow cylinder having a central axis, whereby stretching in the direction of said central axis is inhibited.

5. A lead, as claimed in claim 4, wherein said support members comprise raised beads arranged parallel to said central axis.

6. A lead, as claimed in claim 5, wherein said beads are integrally formed with said core.

7. A lead, as claimed in claim 5, wherein said wire is coiled around said beads.

8. A lead, as claimed in claim 7, wherein said wire is covered by insulation.

9. A lead, as claimed in claim 8, wherein said insulation is sealed to said beads.

10. A lead, as claimed in claim 9, wherein said insulation is heat sealed to said beads.

11. A lead, as claimed in claim 1, wherein said body generally defines a helix having convolutions arranged in a first direction and having a central axis, whereby stretching of said lead in the direction of said central axis is facilitated.

12. A lead, as claimed in claim 11, wherein said wire is wound around said body to form convolutions arranged in a second direction opposite said first direction.

13. A lead, as claimed in claim 11, wherein said wire is covered by insulation.

14. A lead, as claimed in claim 13, wherein said insulation is sealed to said convolutions.

15. A lead, as claimed in claim 14, wherein said insulation is heat sealed to said body.

16. A lead, as claimed in claim 14, wherein said insulation is solvent bonded to said body.

17. A lead, as claimed in claim 14, wherein said insulation is bonded to said body with adhesives.

18. A lead, as claimed in claim 1, wherein said wire is unyielded wire.

19. A lead, as claimed in claim 18, wherein said wire is multistranded.

* * * * *